United States Patent [19]

Andrew

[11] Patent Number: 4,973,312

[45] Date of Patent: Nov. 27, 1990

[54] METHOD AND SYSTEM FOR INSERTING SPINAL CATHETERS

[76] Inventor: Daniel E. Andrew, 524 Beechwood Dr., Unit 34, Waterloo, Ontario N2T 2G9, Canada

[21] Appl. No.: 357,502

[22] Filed: May 26, 1989

[51] Int. Cl.$^5$ ............................................. A61M 5/18
[52] U.S. Cl. ..................................... 604/158; 604/165
[58] Field of Search ................. 604/158, 163, 164, 165

[56] References Cited

U.S. PATENT DOCUMENTS 4,192,305  3/1980  Seberg ................................... 604/165
4,362,156 12/1982  Feller, Jr. et al. .................... 604/165

Primary Examiner—John D. Yasko
Attorney, Agent, or Firm—Arne I. Fors

[57] ABSTRACT

A method and a system for inserting spinal catheters for administration of spinal anaesthesia are disclosed. An epidural needle having a hub is inserted into the epidural space of a patient and a cannula having a blunt end is inserted into and advanced forwardly within the epidural needle for abutment against the dura-arachnoid membrane to place the membrane in tension. The cannula is locked in place in the epidural needle by a securing means attached to the hub of the epidural needle. A flexible catheter having a wire or stylet therein with an end projecting beyond the distal end of the catheter is inserted through the cannula for piercing a hole in the tensioned dura-arachnoid membrane whereby the catheter can be inserted a predetermined distance through the dura-arachnoid membrane into the subarachnoid space. The cannula and epidural needle are removed and the wire withdrawn to allow continuous administering of an anaesthetic through the catheter. A hole can be formed in the dura-arachnoid membrane by a sharp stylet prior to insertion of the catheter.

8 Claims, 6 Drawing Sheets

METHOD AND SYSTEM FOR INSERTING SPINAL CATHETERS

BACKGROUND OF THE INVENTION

1. Field of the Invention

This invention relates to the field of catheters and, more particularly, relates to a method and to a system for inserting catheters for administering spinal anaesthesia.

2. Description of the Prior Art

Catheter placement devices and related methods involve puncturing of a membrane or like tissue by means of a hollow needle within which a catheter is introduced to the desired location, and the needle and related accessories removed leaving the catheter in place. The hole formed in the tissue by the needle usually is larger than the diameter of the catheter allowing fluids to leak from one side of the membrane to the other to cause severe discomfort to the patient. U.S. Pat. No. 4,417,886 issued Nov. 29, 1983 discloses a catheter introduction set for introducing a catheter into a small diameter blood vessel consisting of a catheter mounted on a hollow needle having a spring wire guide therein. In use, the hollow needle is first inserted into the blood vessel, the spring wire guide is advanced into the blood vessel as far as possible and the catheter then advanced on the spring wire guide into the blood vessel. The spring wire guide and needle are removed leaving the catheter in the blood vessel.

U.S. Pat. No. 4,655,750 issued Apr. 7, 1987 discloses another embodiment of catheter system for placement of a flexible catheter into the lumen of an artery or vein which includes a guide wire adapted to be advanced into the lumen and a catheter advanced along the guide wire until placement is achieved.

U.S. Pat. No. 4,529,399 issued July 16, 1985 discloses a method and apparatus for placing a catheter in which a hole is made in a vessel wall by a needle outside a catheter and the catheter advanced on a stylet.

Epidural and spinal anaesthesia require the administration of an anaesthetic agent into the epidural or subarachnoid spaces respectively of the spine. Epidural anaesthesia requires substantially more anaesthetic agent than spinal anaesthesia and, if the anaesthetist inadvertently penetrates the duraarachnoid membrane while endeavouring to administer an anaesthetic agent to the epidural space, a dangerous quantity of anaesthetic agent can be placed in the subarchnoid space, possibly causing paralysis or even death.

U.S. Pat. No. 4,518,383 issued May 21, 1985 teaches an instrument for epidural and spinal anaesthesia in which an outer hollow Tuohy TM needle has a bent pointed tip to locate the epidural space and an inner hollow needle with a pointed tip projecting forwardly of the outer Tuohy TM needle in alignment therewith to penetrate the dura with a minimum of cutting of tissue.

U.S. Pat. No. 4,737,146 issued Apr. 12, 1988 discloses another version of epidural catheter in which a rigid epidural needle is inserted into an epidural space and an epidural catheter is introduced through the needle into the epidural space through a lateral opening in the tip of the needle.

It is an object of the present invention to provide a method and system for inserting a spinal catheter to ensure correct placement of the catheter in the subarachnoid space and to obviate leakage of cerebrospinal fluid from the subarachnoid space into the epidural space of the spine during and after administration of continuous spinal anaesthesia.

BRIEF SUMMARY OF THE INVENTION

In accordance with one aspect of the catheter system of the invention, for the insertion of a flexible catheter through the epidural space and dura-arachnoid membrane into the subarachnoid space of a spine, the system comprises a hollow needle having a sharpened entry end for insertion into the epidural space and an exit end having a hub, a cannula with a blunt distal end adapted for placement into and axial movement within the hollow needle whereby said cannula can be advanced forwardly within the hollow needle for abutment of the blunt distal end against the dura-arachnoid membrane to place tension on the dura-arachnoid membrane, securing means adapted to be attached to the hub at the exit end of the hollow needle for locking the cannula within the hollow needle from axial movement, and a flexible catheter having a wire therein for insertion through the cannula and penetrating the dura-arachnoid membrane forming a hole, whereby the distal end of the catheter can be inserted a predetermined distance into the subarachnoid space through said hole, the cannula and the hollow needle retracted along the catheter, the securing means removed, and the wire withdrawn from the catheter.

In accordance with an aspect of the method of the invention for passing a catheter through the epidural space and dura-arachnoid membrane into the subarachnoid space of a patient's spine, the method comprises the steps of inserting a hollow needle having a sharpened entry end into the epidural space, said hollow needle having an exit end with a hub, inserting a cannula with a blunt distal end into the hollow needle and advancing the cannula forward for abutment of the blunt distal end of the cannula against the dura-arachnoid membrane to place the dura-arachnoid membrane in tension, locking the cannula from coaxial movement in the needle, inserting a flexible catheter having a wire therein through the cannula and penetrating the tensioned dura-arachnoid membrane through a hole therein whereby the distal end of the catheter can be fed a predetermined distance into the subarachnoid space through the hole formed in the dura-arachnoid membrane, and retracting the hollow needle and cannula along the catheter and withdrawing the wire while the distal end of the catheter remains inserted in the said subarachnoid space.

In accordance with another aspect of the present invention, the dura-arachnoid can be pierced with a sharp stylet to form a hole prior to insertion of the catheter with a wire.

BRIEF DESCRIPTION OF THE DRAWINGS

The method and apparatus of the invention will now be described with reference to the accompanying drawings, in which.

DESCRIPTION OF THE PREFERRED EMBODIMENTS

Figure 1:
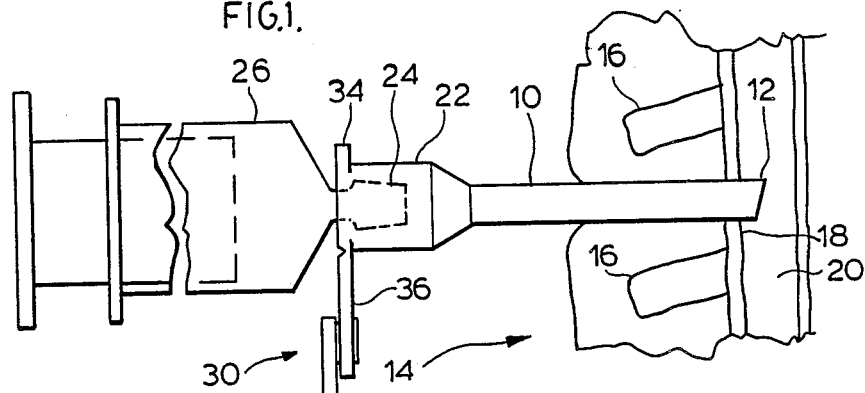
FIG. 1 is an elevation of an epidural needle, with syringe, inserted into the epidural space of a spine.

FIG. 1 of the drawings illustrates the placement of a hollow epidural needle 10 having a sharpened end 12 inserted into the back 14 of a patient between the spinous processes 16 of the vertebrae and through the ligamentum flavum 18 into the epidural space 20. The opposite end of needle 10 has a hub 22 having a conventional conical interior for receiving the forward extension 24 of a syringe 26 and a pivot clamp or the like connector 30 shown in more detail in FIGS. 10, 11 and 12.

Figure 10:
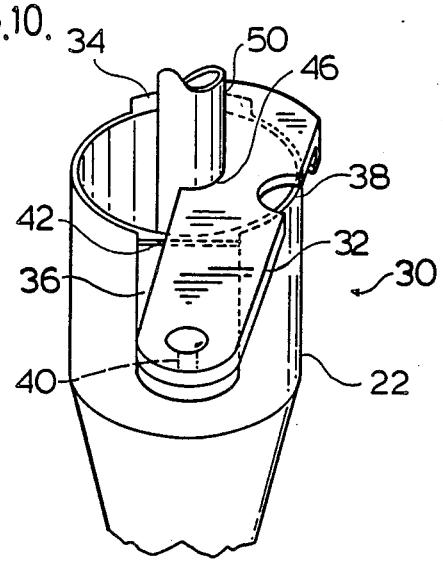
FIG. 10 is a perspective view in more detail of the hub of the epidural needle showing the clamp engaging the cannula.
Figure 11:
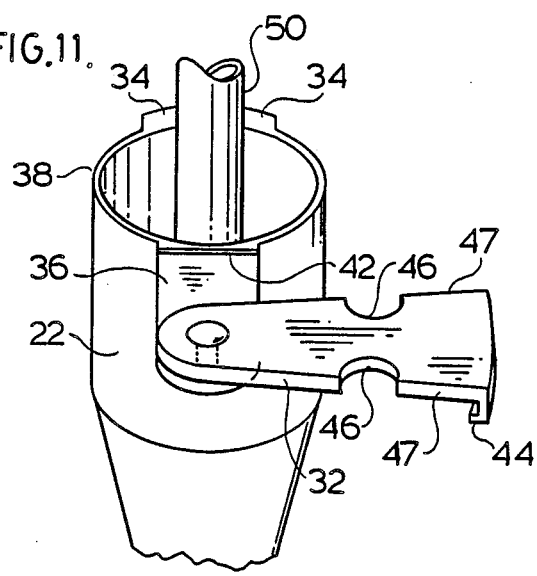
FIG. 11 is a perspective view of the circular clamp illustrated in FIG. 10 released from the cannula.
Figure 12:
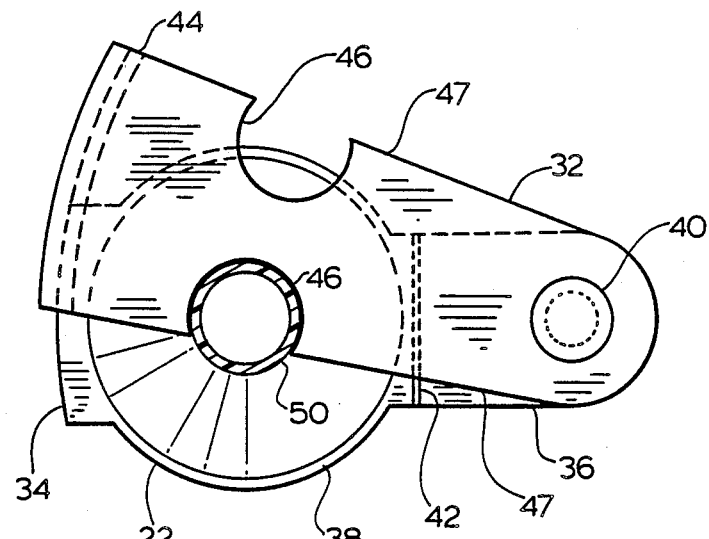
FIG. 12 is a plan view of the clamp in its locking position corresponding to FIG. 10.

With reference now to FIGS. 10, 11 and 12, pivot clamp 30 comprises a clamp arm 32 pivotally mounted on lateral extension or tab 36 formed adjacent the edge 38 of hub 22 by a stud 40. A transverse line of weakness 42 is formed in tab 36 to permit separation of tab 36 from hub 22 for reasons which will become apparent as the description proceeds.

Figure 4:
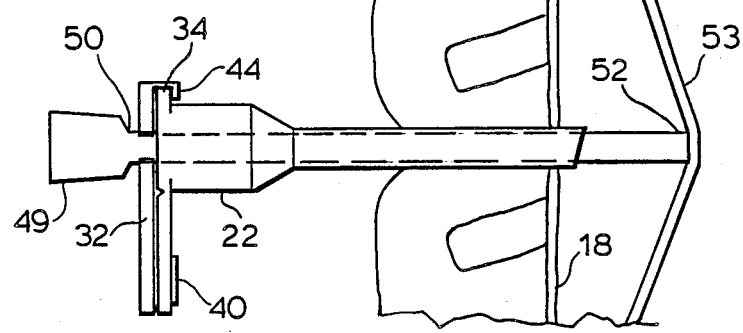
FIG. 4 is an elevation showing the cannula advanced and locked in place by a clamp.

Clamp arm 32 has a peripheral reverse flange 44 adapted to overlap and engage flange 34 of hub 22 when clamp 32 is pivotted to the operative position shown in FIGS. 4, 10 and 12. An opening 46 on each of side edge 47 of clamp arm 32 defines slightly more than a semicircle with a diameter substantially equal to the diameter of a cannula, to be described, whereby the clamp arm 32 can be snap-fitted over the cannula for frictional engagement, as shown most clearly in FIGS. 10 and 12.

Figure 2:
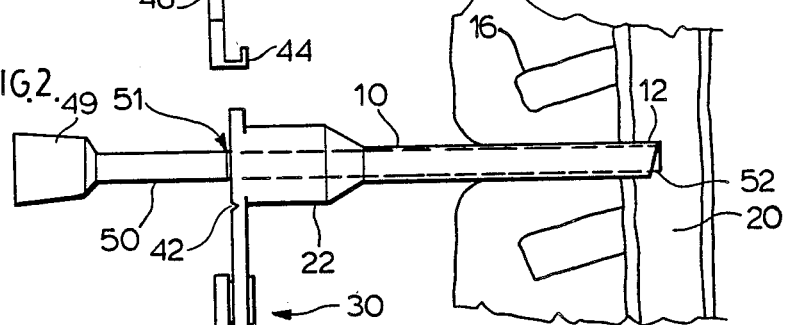
FIG. 2 is an elevation showing a cannula inserted into the epidural needle.

With reference now to FIG. 2, cannula 50 having a blunt distal end 52 and a hub 49 at the proximal end has a diameter slightly less than the interior diameter of the needle 10 to allow placement into and coaxial movement within needle 10 such that the distal end 52 of cannula 50 can be advanced forwardly for alignment with the end 12 of needle 10 when mark 51 on the cannula is aligned with the end of needle hub 22.

Figure 3:
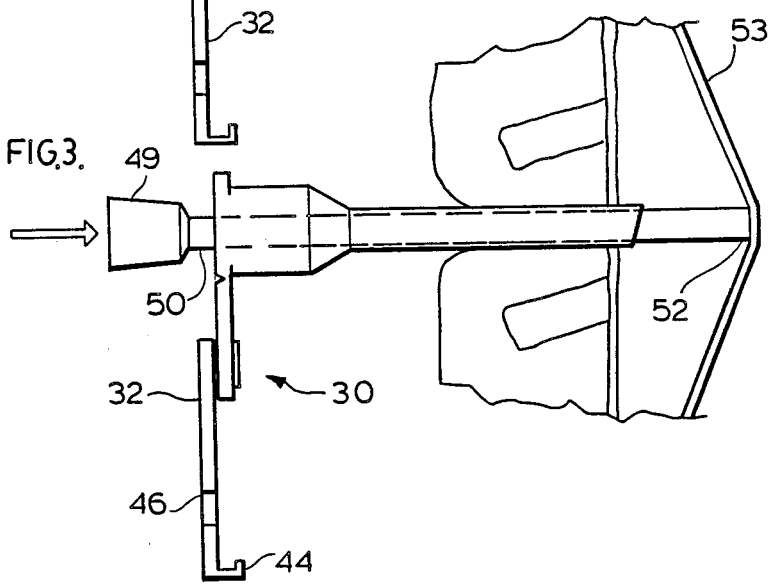
FIG. 3 is an elevation showing the cannula extended to tension the dura-arachnoid membrane.

With reference now to FIGS. 3 and 4, cannula 50 with blunt end 52 is advanced forwardly to place dura-arachnoid membrane 53 in tension and the cannula locked from axial movement by pivoting clamp arm 32 upwardly as 25 viewed in FIGS. 4-9 of the drawings such that cannula 50 is frictionally engaged by the wall of an opening 46 when clamp arm 32 is snap-fitted thereover with reverse flange 44 engaging flange 34 of needle hub 22.

Figure 5:
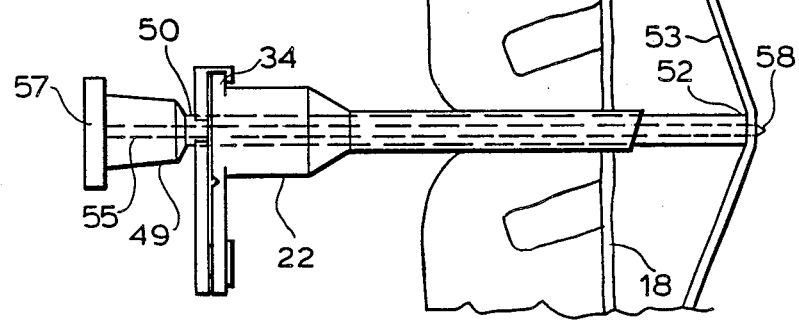
FIG. 5 is an elevation showing a sharply pointed stylet inserted into the cannula for piercing the dura-arachnoid membrane.
Figure 6:
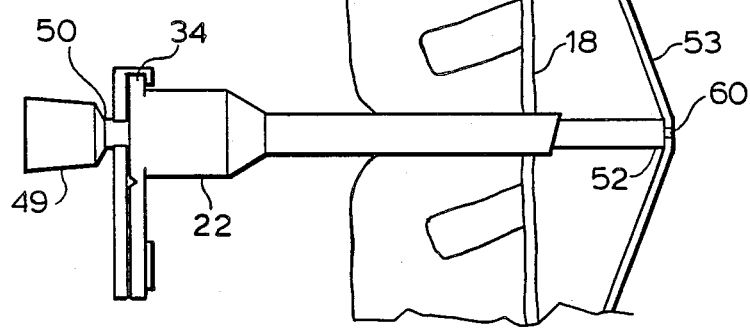
FIG. 6 is an elevation showing a hole pierced in the dura-arachnoid membrane.

FIG. 5 illustrates a sharp stylet 55 advanced through cannula 50 to pierce the taut dura-arachnoid membrane 53 by pointed tip 58 when flanged head 57 abuts the end of hub 49 of cannula 50 to form a hole 60 (FIG. 6). Stylet 55 preferably would have a diameter about the same as or slightly less than the external diameter of catheter 54 to ensure a tight fit of the catheter in hole 60 to prevent the flow of cerebral-spinal fluid from the sub-arachnoid space into the epidural space.

Figure 7:
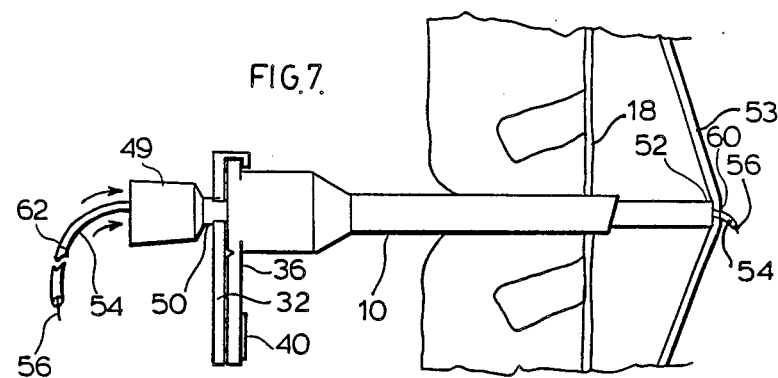
FIG. 7 is an elevation showing a catheter with a wire slidably inserted therein penetrating a hole in the dura-arachnoid membrane, the end of the wire protruding slightly beyond the end of the catheter.
Figure 8:
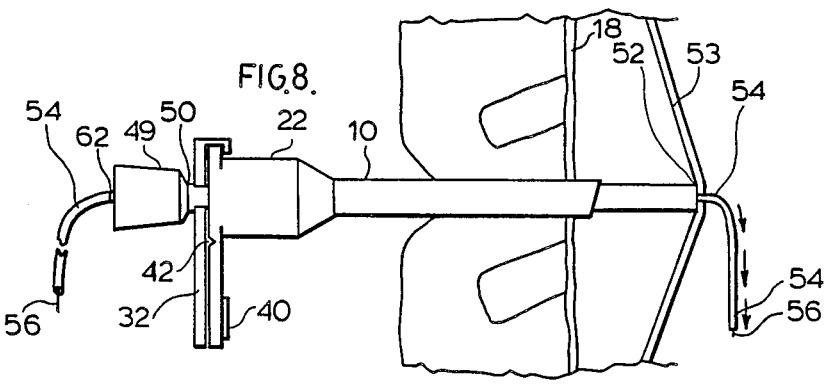
FIG. 8 depicts the advance of the catheter with the wire a desired distance into the subarchnoid space, as indicated by a mark on the catheter.

A catheter 54 with an interior wire 56 slidably mounted therein having an end projecting beyond the forward end of catheter 54 is inserted into cannula 50 and advanced forwardly to enter hole 60, as shown in FIG. 7. Catheter 54 can be advanced through hole 60 in dura-arachnoid membrane 53 a desired length as indicated by mark 62 on the catheter by pushing catheter 54 with stiffening wire 56 forwardly through the dura-arachnoid membrane 53 until mark 62 on cather 54 is aligned with the proximal end of cannula hub 49, as shown in FIG. 8.

It may be preferred not to use stylet 55, in which case wire 56 would be sharply pointed and would extend beyond the tip of catheter 54 to pierce the dura-arachnoid membrane 53 when catheter 54 is advanced against membrane 53.

Figure 9:
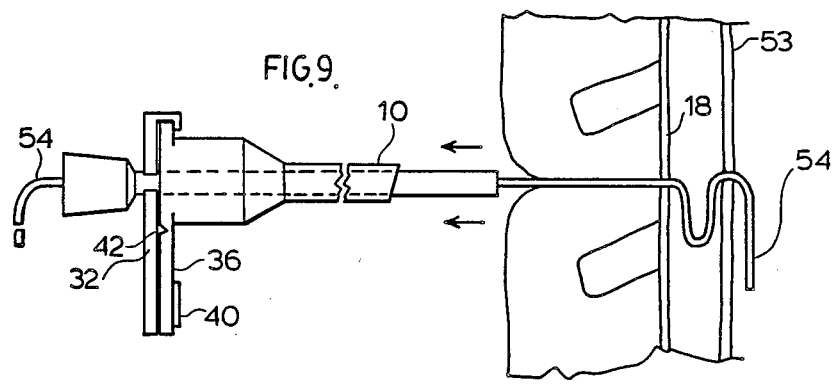
FIG. 9 is an elevation showing the withdrawal of the cannula with epidural needle, and wire, from the patient with the catheter left in site.
Figure 13:
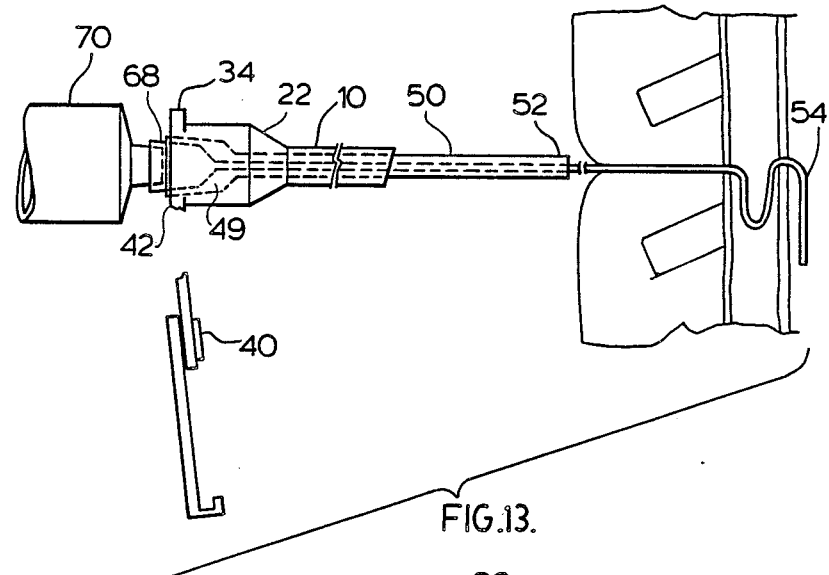
FIG. 13 is an elevation of the cannula and epidural needle frictionally connected together at the hub end of the catheter, the clamp separated from the hub of the epidural needle, and with a syringe inserted into the catheter hub.

When the catheter 54 has been extended to its desired length into the subarachnoid space through the dura-arachnoid membrane 53, as indicated by lining up mark 62 on catheter 54 with the proximal end of hub 49 of cannula 50, epidural needle 10 with cannula 50 attached thereto by clamp 32 is removed from the patient, with the catheter 54 remaining in position, as typified in FIG. 9. With reference now to FIG. 13, clamp 32 is removed from cannula 50 and is then broken at line of weakness 42, when desired, for removal of said clamp, the hub 49 of cannula 50 is advanced into the hub 22 of epidural needle 10, and needle 10 with cannula 50 nested therein is retracted to receive the hub 68 of catheter 54 at the free end of catheter 54. A sufficient length of catheter 54 is provided to permit taping of the catheter to the patient with the epidural needle and cannula connected together in such a manner that the cannula prevents the catheter from being cut by the sharp end of the needle.

An anaesthetic can be continuously administered to the patient through the catheter 54 by syringe 70 which is coupled either directly or by means of an extension tubing to hub 68 of catheter 54 which is fitted tightly into the hub 49 of cannula 50.

Figure 14:
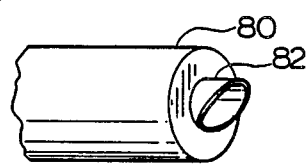
FIG. 14 is an enlarged view of the end of another embodiment of cannula.

FIG. 14 illustrates an embodiment of cannula in which the blunt distal end 80 has an inner bevelled, i.e. sharp, extension to pierce the dura-arachnoid membrane while maintaing the membrane taut.

Figure 15:
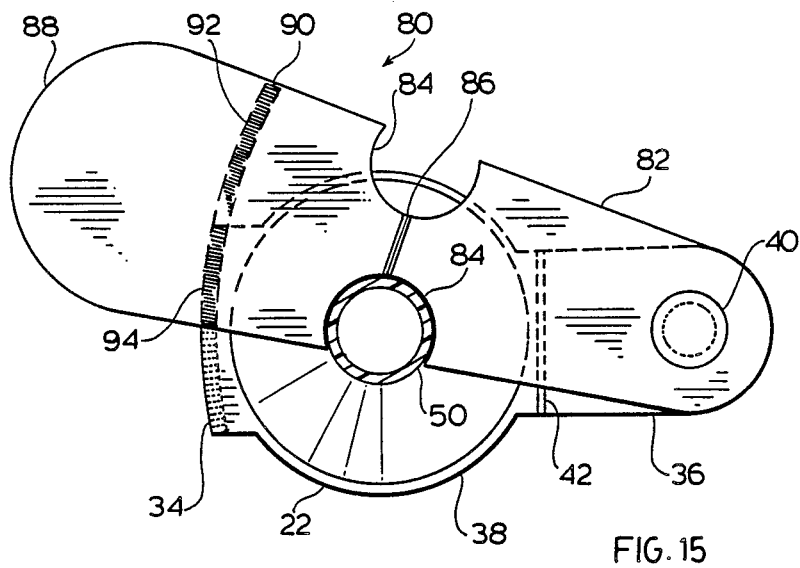
FIG. 15 is a plan view of another embodiment of pivot clamp.
Figure 16:
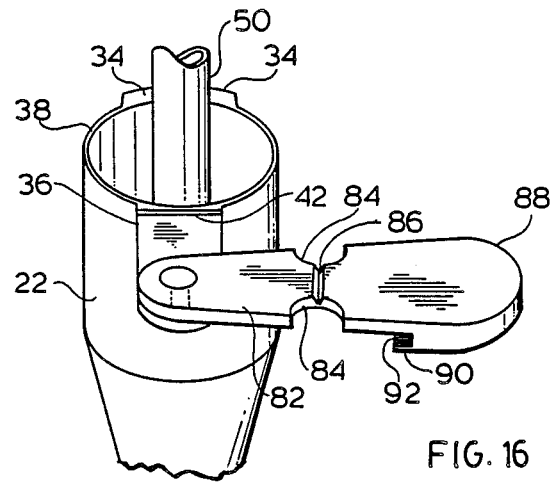
FIG. 16 is a perspective view of the pivot clamp shown in FIG. 15.

FIG. 15 and 16 illustrate another embodiment of pivot clamp 80 in which clamp arm 82, having over-centre semi-circular side openings 84 adapted to snap-fit onto cannula 50, has a transverse line of weakness formed by surface notch 86 interconnecting openings 84. The free end 88 of clamp arm 82 is extended to provide leverage to facilitate the breaking of clamp arm 82 to free cannula 50, when desired.

Reverse flange 90 formed in the underside of clamp arm 82 preferably has serrations 92 adapted to engage mating serrations 94 formed in the underside of rim flange 34 to effectively lock clamp 80 against cannula 50 by a friction fit of cannula 50 in an opening 84.

It will be understood that modifications can be made in the embodiment of the invention illustrated and described herein without departing from the scope and purview of the invention as defined by the appended claims.

I claim:

1. A catheter system for the insertion of a flexible catheter through the epidural space and dura-arachnoid membrane into the subarachnoid space of the spine of a patient comprising:
    (a) a hollow needle having a sharpened tip, for insertion into the epidural space, and an exit end having a hub;
    (b) a cannula with a blunt distal end adapted for placement into and for coaxial movement within the hollow needle, whereby said cannula can be advanced forwardly within the hollow needle for abutment of the blunt distal end against the dura-arachnoid membrane to place the dura-arachnoid membrane in tension;
    (c) securing means adapted to be attached to the hub at the exit end of the hollow needle for locking the cannula within the hollow needle from coaxial movement therein; and
    (d) a flexible catheter having a wire therein for insertion through the cannula and for penetrating the dura-arachnoid membrane, whereby the distal end of the catheter can be inserted a predetermined distance through the dura-arachnoid membrane into the subarachnoid space, the cannula and the hollow needle retracted along the catheter, and the wire withdrawn from the catheter.

2. A catheter system as claimed in claim 1 in which the wire extends beyond the distal end of the catheter and said end of the wire extending beyond the distal end of the catheter is sharpened.

3. A catheter system as claimed in claim 1 in which the securing means comprises a clamp pivotally mounted on a lateral extension of the hub of the hollow needle, said clamp having an opening formed on a side thereof from frictionally engaging and locking the cannula from coaxial movement in the hollow needle.

4. A catheter system as claimed in claim 3 in which said lateral extension of the hub has a line of weakness formed therein adjacent the hub to permit separation of the lateral extension from the hub.

5. A method for passing a catheter through the epidural space and dura-arachnoid membrane into the subarachnoid space of the spine of a patient comprising the steps of:
    (a) inserting a hollow needle having a sharpened tip into the epidural space, said hollow needle having an exit end with a hub;
    (b) inserting a cannula having a distal end into the hollow needle and advancing the cannula forwardly coaxially within the needle for abutment of the distal end of the cannula against the dura-arachnoid membrane for placing the dura-arachnoid membrane in tension, and locking the cannula from coaxial movement in the needle;
    (c) inserting a flexible catheter having a stiffening wire therein through the cannula for penetrating the tensioned dura-arachnoid membrane whereby the distal end of the catheter can be fed a predetermined distance into the subarachnoid space;
    (d) retracting the hollow needle and cannula along the catheter while the catheter remains inserted in the said subarachnoid space with the stiffening wire; and
    (e) removing the stiffening wire.

6. A method as claimed in claim 5 in which the dura-arachnoid membrane is pierced with a stylet prior to insertion of the catheter with stiffening wire.

7. A method for passing a catheter through the epidural space and dura-arachnoid membrane into the subarachnoid space of the spine of a patient comprising the steps of:
    (a) inserting a hollow needle having a sharpened tip into the epidural space, said hollow needle having an exit end with a hub;
    (b) inserting a cannula with a blunt forward end into the hollow needle and advancing the cannula forwardly coaxially within the needle for abutment of the blunt distal end of the cannula against the dura-arachnoid membrane for placing the dura-arachnoid membrane in tension, and locking the cannula from coaxial movement in the needle;
    (c) inserting a flexible catheter having a stiffening wire therein with an end of the wire extending beyond the distal end of the catheter coaxially through the cannula for penetrating the tensioned dura-arachnoid membrane whereby the distal end of the catheter can be fed a predetermined distance into the subarachnoid space, through a hole formed in the dura-arachnoid membrane;
    (d) advancing the catheter a further predetermined distance over the wire into the subarachnoid space through the hole in the dura mater; and
    (e) retracting the hollow needle and cannula along the catheter while the catheter remains inserted in the said subarachnoid space with the stiffening wire; and
    (f) removing the stiffening wire.

8. A method as claimed in claim 7 in which the dura-arachnoid membrane is pierced with a stylet prior to insertion of the catheter with stiffening wire.

* * * * *